(12) United States Patent
O'Neal et al.

(10) Patent No.: US 7,521,395 B2
(45) Date of Patent: Apr. 21, 2009

(54) SYNERGISTICALLY ACTING HERBICIDAL MIXTURES

(75) Inventors: William B. O'Neal, Chapel Hill, NC (US); Elmar Kibler, Haβloch (DE); Dan E. Westberg, Cary, NC (US); Matthias Witschel, Bad Dükheim (DE); Herve R. Vantieghem, Basking Ridge, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 579 days.

(21) Appl. No.: 10/521,806

(22) PCT Filed: Jul. 22, 2003

(86) PCT No.: PCT/EP03/07992

§ 371 (c)(1),
(2), (4) Date: Jan. 21, 2005

(87) PCT Pub. No.: WO2004/008849

PCT Pub. Date: Jan. 29, 2004

(65) Prior Publication Data

US 2005/0256002 A1    Nov. 17, 2005

Related U.S. Application Data

(60) Provisional application No. 60/397,023, filed on Jul. 22, 2002.

(51) Int. Cl.
| | |
|---|---|
| A01N 43/64 | (2006.01) |
| A01N 43/00 | (2006.01) |
| A01N 43/66 | (2006.01) |
| A01N 63/00 | (2006.01) |
| A01N 43/653 | (2006.01) |

(52) U.S. Cl. ..................... 504/134; 504/139
(58) Field of Classification Search ............ 504/116, 504/118, 132, 134, 136, 137, 139, 211; 424/401
See application file for complete search history.

(56) References Cited

U.S. PATENT DOCUMENTS

| 4,789,393 A | 12/1988 | Hanagan |
| 5,846,907 A | 12/1998 | von Deyn et al. |
| 5,939,360 A | 8/1999 | Adachi et al. |
| 6,534,444 B1 * | 3/2003 | Sievernich et al. .......... 504/128 |
| 2002/0025910 A1 | 2/2002 | Deyn et al. |

FOREIGN PATENT DOCUMENTS

| CA | 2334955 A1 * | 12/1999 |
| CN | 1147897 A | 4/1997 |
| WO | WO 97/41116 A1 | 4/1996 |
| WO | WO 97/41117 A1 | 4/1996 |

* cited by examiner

*Primary Examiner*—John Pak
*Assistant Examiner*—Andriae M Holt
(74) *Attorney, Agent, or Firm*—Rothwell, Figg, Ernst & Manbeck, P.C.

(57) ABSTRACT

A synergistic herbicidal mixture comprising
A) at least one 3-heterocyclyl-substituted benzoyl derivative of the formula I

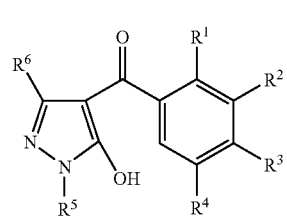

in which the variables have the following meanings: $R^1$, $R^3$ are halogen, alkyl, haloalkyl, alkoxy, haloalkoxy, alkylthio, alkylsulfinyl or alkylsulfonyl; $R^2$ is a optionally substituted heterocyclic radical selected from the group: isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl; $R^4$ is hydrogen, halogen or alkyl; $R^5$ is alkyl, $R^6$ is hydrogen or alkyl; or one of its environmentally compatible salts;
B) nicosulfuron (II) or one of its environmentally compatible salts; and
C) at least one herbicidal compound from the group triazines or one of their environmentally compatible salts, in a synergistically effective amount. Compositions comprising these mixtures, processes for the preparation of these compositions, and their use for controlling undesirable plants.

9 Claims, No Drawings

SYNERGISTICALLY ACTING HERBICIDAL MIXTURES

CROSS REFERENCE TO RELATED APPLICATION

This application is a 35 USC § 371 National Phase Entry Application from PCT/EP2003/007992, filed Jul. 22, 2003, and designating the U.S., which claims the benefit of U.S. Ser. No. 60/397,023 filed Jul. 22, 2002.

The present invention relates to a synergistic herbicidal mixture comprising

A) at least one 3-heterocyclyl-substituted benzoyl derivative of the formula I in which the variables have the following meanings:

$R^1$, $R^3$ are halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkyl-sulfinyl or $C_1$-$C_6$-alkylsulfonyl;

$R^2$ is a heterocyclic radical selected from the group: isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, it being possible for the six radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^4$ is hydrogen, halogen or $C_1$-$C_6$-alkyl;

$R^5$ is $C_1$-$C_6$-alkyl;

$R^6$ is hydrogen or $C_1$-$C_6$-alkyl;

or one of its environmentally compatible salts; and

B) the compound of formula II or one of its environmentally compatible salts; and C) at least one herbicidal compound from the group of the acetolactate synthase inhibitors (ALS), lipid biosynthesis inhibitors and photosynthesis inhibitors;

in a synergistically effective amount.

The invention furthermore relates to herbicidal compositions comprising a herbicidally active amount of a synergistic herbicidal mixture as defined above and at least one liquid and/or solid carrier and, if desired, at least one surfactant.

Moreover, the invention relates to processes for the preparation of these compositions and to a method of controlling undesirable vegetation.

In crop protection products, it is always desirable to increase the specific activity of an active ingredient and the reliability of action. It is an object of the present invention to increase the activity and/or selectivity of the herbicidally active 3-heterocyclyl-substituted benzoyl derivatives of the formula I against undesirable harmful plants.

We have found that this object is achieved by the mixtures defined at the outset. We have furthermore found herbicidal compositions which comprise these mixtures, processes for their preparation, and methods of controlling undesirable vegetation. In the last-mentioned cases, it is irrelevant whether the herbicidally active compounds of the components A), B) and C) are formulated and applied jointly or separately and in which sequence they are applied in the case of separate application.

The mixtures according to the invention show a synergistic effect; the compatibility of the herbicidally active compounds of components A), B) and C) for certain crop plants is generally retained.

Suitable components C are, as acetolactate synthase inhibitors (ALS), inter alia, imidazolinones, pyrimidyl ethers, sulfonamides or sulfonyl ureas. Lipid biosynthesis inhibitors which are used are, inter alia, anilides, chloroacetanilides, thioureas, benfuresate or perfluidone. Suitable photosynthesis inhibitors are, inter alia, propanil, pyridate, pyridafol, benzothiadiazinones, dinitrophenols, dipyridylenes, ureas, phenols, chloridazon, triazine, triazinone, uracils or biscarbamates.

Examples of herbicides which can be used in combination with the 3-heterocyclyl-substituted benzoyl derivatives of formula I and the compound of formula II according to the present invention are, inter alia:

C1 acetolactate synthase inhibitors (ALS), for example imidazolinones, such as imazapyr, imazaquin, imazamethabenz-methyl (imazame), imazamox, imazapic, imazethapyr or imazamethapyr;

pyrimidyl ethers, such as pyrithiobac-acid, pyrithiobac-sodium, bispyribac-sodium, KIH-6127 or pyribenzoxym;

sulfonamides, such as florasulam, flumetsulam or or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]-carbonyl]-2-(trifluoromethyl)-benzenesulfonamide, sulfosulfuron or iodosulfuron;

C2 lipid biosynthesis inhibitors, for example anilides, such as anilofos or mefenacet;

chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;

thioureas, such as butylate, cycloate, di-allate, dimepiperate, EPTC, esprocarb, molinate, pebulate, prosulfocarb, thiobencarb (benthiocarb), tri-allate or vernolate; or benfuresate or perfluidone;

C3 photosynthesis inhibitors, for example
propanil, pyridate or pyridafol;
benzothiadiazinones, such as bentazone;
dinitrophenols, for example bromofenoxim, dinoseb, dinoseb-acetate, dinoterb or DNOC;
dipyridylenes, such as cyperquat-chloride, difenzoquat-methylsulfate, diquat or paraquat-dichloride;
ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
phenols, such as bromoxynil or ioxynil;
chloridazon;
triazines, such as ametryn, atrazine, cyanazine, desmetryn, dimethamethryn, hexazinone, prometon, prometryn, propazine, simazine, simetryn, terbumeton, terbutryn, terbutylazine or trietazine;
triazinones, such as metamitron or metribuzin;
uracils, such as bromacil, lenacil or terbacil, or
biscarbamates, such as desmedipham or phenmedipham;
or their environmentally compatible salts.

The 3-heterocyclyl-substituted benzoyl derivatives of the formula I are disclosed in WO 96/26206, WO 97/41116, WO 97/41117 and WO 97/41118, WO 98/31681.

The compound of formula II (common name nicosulfuron) is disclosed in U.S. Pat. No. 4,789,393.

The herbicidally active compounds from amongst groups C1 to C3 are described, for example, in "Herbizide [Herbicides]", Hock, Fedtke, Schmidt, 1$^{st}$ edition, Thieme 1995 (s. "molinate" p. 32, "butachlor" p. 32, "mefenacet" p. 32, "dimepiperate" p. 32, "bensulfuronmethyl" p. 31, "pyrazosulfuron-ethyl" p. 31, "cinosulfuron" p. 31, "benfuresate" p. 233, "dimethyametryn" p. 118, "esprocarb" p. 229, "propanil" p. 32, "bentazon" p. 30, "azimsulfuron (DPX-A-8947)" p. 175, "metosulam" p. 33, "lethametsulfuron- methyl" p. 36, "thifensulfuron-methyl" p. 35, "pyrithiobac acid" p. 181);

"Agricultural Chemicals", Book II Herbicides, 1993 (s. "thiobencarb" p. 85, "imazosulfuron (TH-913)" p. 150, "dimethenamid" p. 48, "anilofos" p. 241, "bromofenoxim" p. 228, "prosulfocarb" p. 84, "metazachlor" p. 64, "imazamethabenz-methyl" p. 153, "pyrithiobac-sodium" p. 266, "flumetsulam" p. 227, "amidosulfuron" p. 151, "halosulfuron-methyl" p. 148, "rimsulfuron" p. 138, "tribenuron-methyl" p. 139, "triflusulfuron-methyl" p. 137, "primisulfuron-methyl" p. 147);

"Agricultural Chemicals", Book II Herbicides, 13$^{th}$ Edition (s. "sulfosulfuron" p. 145, "ethoxy-sulfuron" p. 149, "pyribenzoxym" p. 279, "imazapic" p. 160, "butenachlor" p. 54);

"Short Review of Herbicides & PGRs 1991, Hodogaya Chemicals (s. "thenylchlorid (NSK-850)" p. 52, "butylate" p. 106, "cycloate" p. 108, "desmedipham" p. 104, "desmetryne" p. 200, "di-allate" p. 106, "EPTC" p. 108, "pebulate" p. 106, " phenmedipham" p. 104, "tri-allate" p. 108, "vernolate" p. 108, "acetochlor" p. 48, "alachlor" p. 46, "difenoxuron" p. 76, "diethathyl-ethyl" p.48, "dimethachlor" p. 50, "metolachlor" p. 46, "propachlor" p. 44, "pyrnachlor" p. 44, "terbuchlor" p. 48, "xylachlor" p. 52, "dinoseb" p. 128, "dinoseb-acetate" p. 128, "dinoterb" p. 128; "DNOC" p. 126, "cyperquat-chloride" p. 158, "difenzoquat-methylsulfate" p. 160, "diquat" p. 158, "paraquat-dichloride" p. 158, "chlorobromuron" p. 72, "chlorotoluron" p. 74, "dimefuron" p. 88, "diuron" p. 70, "ethidimuron" p. 86, "fenuron" p. 64, "fluometuron" p. 68, "isoproturon" p. 80, "isouron" p. 88, "linuron" p. 72, "methabenzthiazuron" p. 82, "metoxuron" p. 72, "monolinuron" p. 66, "neburon" p. 72, "siduron" p. 68, "tebuthiuron" p. 86, "imazamethapyr" p. 172, "imazapyr" p. 170, "imazaquin" p. 170, "imazethapyr" p. 172, "methazole" p. 162, "bromoxynil" p. 148, "ioxynil" p. 148, p. 18, "chloridazon" p. 174, "pyridate" p. 176, "chlorimuron-ethyl" p. 92, "chlorsulfuron" p. 92, "flazasulfuron" p. 96, "metsulfuron-methyl" S.92, "nicosulfuron" p. 96, "sulfometuron-methyl" p. 92, "tria-sulfuron" p. 94, "ametryn" p. 198, "atrazine" p. 188, "cyanazine" p. 192, "hexazinone" p. 208, "prometone" p. 196, "prometryn" p. 196, "propazine" p. 188, "simazine" p. 188, "simetryn" p. 196, "terbumeton" p. 204, "terbutryn" p. 198, "terbutylazine" p. 190, "trietazine" p. 188, "metamitron" p. 206, "metribuzin" p. 202, "bromacil" p. 180, "lenacil" p. 180, "terbacil" p. 180, "perfluidone" p. 260);

"The Pesticide Maunal, 12$^{th}$ edition, 2000 (s. "bispyribac-sodium" p. 97, "florasulam" p. 420, "cyclosulfamuron" p. 217, "pretiachlor" p. 755);

Moreover, other compounds are known from "Brighton Crop Protection Conference—Weeds—1993" (S. "KIH-6127" p. 47, "prosulfuron" p. 53, "metobenzuron" p. 67) The compound "N-[[[4-methoxy-6-(trifluoromethyl)-1,3,5-triazin-2-yl]amino]-carbonyl]-2-(trifluoromethyl-benzenesulfonamide)" is described in PCT/EP 96/03996.

The assignment of the active ingredients to the respective mechanisms of action is based on current knowledge. If several mechanisms of action apply to one active ingredient, this substance was only assigned to one mode of action.

The 3-heterocyclyl-substituted benzoyl derivatives of the formula I can exist, or be used, in the form of the pure enantiomers and also as racemates or diastereomer mixtures.

The 3-heterocyclyl-substituted benzoyl derivatives of the formula I and/or the compound of formula II and/or the herbicidally active compounds from amoungs groups C1 to C3 may also exist in the form of their environmentally compatible salts. Suitable salts are, in general, the salts of those cations, or the acid addition salts of those acids, whose cations, or anions, respectively, do not adversely affect the herbicidal action of the active ingredients.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-yl ammonium, di(2-hydroxyeth-1-yl)ammonium, trimethylbenzylammonium, furthermore phosphonium ions, sulfonium ions, preferably tri($C_1$-$C_4$-alkyl)sulfonium and sulfoxonium ions, preferably, tri($C_1$-$C_4$-alkyl)sulfoxonium.

Anions of suitable acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$-$C_4$-alkanoic acids, preferably formate, acetate, propionate and butyrate.

Preferred with regard to the synergistic herbicidal action of the mixtures according to the invention are those 3-heterocyclyl-substituted benzoyl derivatives of the formula I in which the variables have the following meanings, either alone or in combination:

$R^1$ halogen such as chlorine or bromine, $C_1$-$C_6$-alkyl such as methyl or ethyl or $C_1$-$C_6$-alkylsulfonyl such as methylsulfonyl or ethylsulfonyl;

especially preferably chlorine, methyl or methylsulfonyl;

$R^2$ a heterocyclic radical selected from the group: isoxazol-3-yl, isoxazol-5-yl and 4,5-dihydroisoxazol-3-yl, it being possible for the three radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

especially preferably isoxazol-5-yl, 3-methyl-isoxazol-5-yl, 4,5-dihydroisoxazol-3-yl, 5-methyl-4,5-dihydroisoxazol-3-yl, 5-ethyl-4,5-dihydroisoxazol-3-yl or 4,5-dimethyl-4,5-dihydroisoxazol-3-yl;

$R^3$ halogen such as chlorine or bromine or $C_1$-$C_6$-alkylsulfonyl such as methylsulfonyl or ethylsulfonyl;

especially preferably chlorine, methylsulfonyl or ethylsulfonyl;

$R^4$ hydrogen or methyl;

especially preferably hydrogen;

$R^5$ is $C_1$-$C_6$-alkyl, such as methyl, ethyl, propyl, 1-methylethyl, butyl, 1-methylpropyl or 2-methylpropyl;

especially preferably methyl, ethyl or 1-methylethyl;

$R^6$ hydrogen or $C_1$-$C_6$ alkyl, such as methyl or ethyl;

especially preferably hydrogen or methyl.

Very particularly preferred are those 3-heterocyclyl-substituted benzoyl derivatives of the formula Ia, in particular the compounds Ia.1 to Ia.47, which are mentioned in Table 1 which follows:

TABLE 1

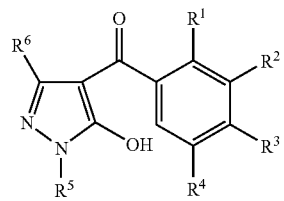

I

| No. | $R^1$ | $R^2$ | $R^3$ | $R^4$ | $R^5$ | $R^6$ |
|---|---|---|---|---|---|---|
| Ia.1 | Cl | 4,5-dihydroisoxazol-3-yl | $SO_2CH_3$ | H | $CH_3$ | $CH_3$ |
| Ia.2 | Cl | 4,5-dihydroisoxazol-3-yl | Cl | H | $CH_3$ | $CH_3$ |
| Ia.3 | Cl | 4,5-dihydroisoxazol-3-yl | $SO_2CH_3$ | H | $CH_3$ | H |
| Ia.4 | Cl | 4,5-dihydro-5-methylisoxazol-3-yl | $SO_2CH_3$ | H | $CH_3$ | H |
| Ia.5 | Cl | 4,5-dihydro-5,5-dimethylisoxazol-3-yl | $SO_2CH_3$ | H | $CH_3$ | H |
| Ia.6 | Cl | 4,5-dihydro-5-ethylisoxazol-3-yl | $SO_2CH_3$ | H | $CH_3$ | H |
| Ia.7 | Cl | 4,5-dihydro-5,5-diethylisoxazol-3-yl | $SO_2CH_3$ | H | $CH_3$ | H |
| Ia.8 | Cl | 4,5-dihydro-5-chloromethylisoxazol-3-yl | $SO_2CH_3$ | H | $CH_3$ | H |
| Ia.9 | Cl | 4,5-dihydro-5-ethoxyisoxazol-3-yl | $SO_2CH_3$ | H | $CH_3$ | H |
| Ia.10 | Cl | 4,5-dihydro-5-methoxyisoxazol-3-yl | $SO_2CH_3$ | H | $CH_3$ | H |
| Ia.11 | Cl | 4,5-dihydro-4,5-dimethylisoxazol-3-yl | $SO_2CH_3$ | H | $CH_3$ | H |
| Ia.12 | Cl | 4,5-dihydro-5-thioethylisoxazol-3-yl | $SO_2CH_3$ | H | $CH_3$ | H |
| Ia.13 | Cl | 4,5-dihydro-5-trifluoromethylisoxazol-3-yl | $SO_2CH_3$ | H | $CH_3$ | H |
| Ia.14 | Cl | 4,5-dihydroisoxazol-3-yl | $SO_2CH_3$ | H | $C_2H_5$ | H |
| Ia.15 | Cl | 4,5-dihydroisoxazol-3-yl | Cl | H | $C_2H_5$ | H |
| Ia.16 | Cl | 4,5-dihydro-5-methylisoxazol-3-yl | $SO_2CH_3$ | H | $C_2H_5$ | H |
| Ia.17 | Cl | 4,5-dihydro-5,5-dimethylisoxazol-3-yl | $SO_2CH_3$ | H | $C_2H_5$ | H |
| Ia.18 | Cl | 4,5-dihydro-5-ethylisoxazol-3-yl | $SO_2CH_3$ | H | $C_2H_5$ | H |
| Ia.19 | Cl | 4,5-dihydro-5,5-diethylisoxazol-3-yl | $SO_2CH_3$ | H | $C_2H_5$ | H |
| Ia.20 | Cl | 4,5-dihydro-5-chloromethylisoxazol-3-yl | $SO_2CH_3$ | H | $C_2H_5$ | H |
| Ia.21 | Cl | 4,5-dihydroisoxazol-3-yl | $SOCH_3$ | H | $C_2H_5$ | H |
| Ia.22 | Cl | 4,5-dihydro-5-ethoxyisoxazol-3-yl | $SO_2CH_3$ | H | $C_2H_5$ | H |
| Ia.23 | Cl | 4,5-dihydro-4,5-dimethylisoxazol-3-yl | $SO_2CH_3$ | H | $C_2H_5$ | H |
| Ia.24 | Cl | 4,5-dihydro-5-thioethylisoxazol-3-yl | $SO_2CH_3$ | H | $C_2H_5$ | H |
| Ia.25 | Cl | 4,5-dihydro-5-trifluoromethylisoxazol-3-yl | $SO_2CH_3$ | H | $C_2H_5$ | H |
| Ia.26 | Cl | 4,5-dihydroisoxazol-3-yl | $SO_2CH_3$ | H | i-$C_4H_9$ | H |
| Ia.27 | $CH_3$ | 4,5-dihydroisoxazol-3-yl | $SO_2CH_3$ | H | $CH_3$ | $CH_3$ |
| Ia.28 | $CH_3$ | 4,5-dihydroisoxazol-3-yl | Cl | H | $CH_3$ | $CH_3$ |
| Ia.29 | $CH_3$ | 4,5-dihydroisoxazol-3-yl | $SO_2CH_3$ | H | $CH_3$ | H |
| Ia.30 | $CH_3$ | 4,5-dihydro-5-methylisoxazol-3-yl | $SO_2CH_3$ | H | $CH_3$ | H |
| Ia.31 | $CH_3$ | 4,5-dihydro-5,5-dimethylisoxazol-3-yl | $SO_2CH_3$ | H | $CH_3$ | H |
| Ia.32 | $CH_3$ | 4,5-dihydro-5-ethylisoxazol-3-yl | $SO_2CH_3$ | H | $CH_3$ | H |
| Ia.33 | $CH_3$ | 4,5-dihydro-5,5-diethylisoxazol-3-yl | $SO_2CH_3$ | H | $CH_3$ | H |
| Ia.34 | $CH_3$ | 4,5-dihydroisoxazol-3-yl | $SO_2CH_3$ | H | $CH_3$ | H |
| Ia.35 | $CH_3$ | 4,5-dihydro-4,5-dimethylisoxazol-3-yl | $SO_2CH_3$ | H | $CH_3$ | H |
| Ia.36 | $CH_3$ | 4,5-dihydroisoxazol-3-yl | $SO_2CH_3$ | H | $C_2H_5$ | H |
| Ia.37 | $CH_3$ | 4,5-dihydroisoxazol-3-yl | Cl | H | $C_2H_5$ | H |
| Ia.38 | $CH_3$ | 4,5-dihydro-5-methylisoxazol-3-yl | $SO_2CH_3$ | H | $C_2H_5$ | H |
| Ia.39 | $CH_3$ | 4,5-dihydro-5,5-dimethylisoxazol-3-yl | $SO_2CH_3$ | H | $C_2H_5$ | H |
| Ia.40 | $CH_3$ | 4,5-dihydro-5-ethylisoxazol-3-yl | $SO_2CH_3$ | H | $C_2H_5$ | H |
| Ia.41 | $CH_3$ | 4,5-dihydro-5,5-diethylisoxazol-3-yl | $SO_2CH_3$ | H | $C_2H_5$ | H |
| Ia.42 | $CH_3$ | 4,5-dihydro-4,5-dimethylisoxazol-3-yl | $SO_2CH_3$ | H | $C_2H_5$ | H |
| Ia.43 | $CH_3$ | 4,5-dihydroisoxazol-3-yl | $SO_2CH_3$ | H | i-$C_4H_9$ | H |

TABLE 1-continued

I

| No. | R¹ | R² | R³ | R⁴ | R⁵ | R⁶ |
|---|---|---|---|---|---|---|
| Ia.44 | Cl | 3-methylisoxazol-5-yl | SO₂CH₃ | H | CH₃ | H |
| Ia.45 | Cl | 3-methylisoxazol-5-yl | SO₂CH₃ | H | C₂H₅ | H |
| Ia.46 | CH₃ | 3-methylisoxazol-5-yl | SO₂CH₃ | H | CH₃ | H |
| Ia.47 | CH₃ | 3-methylisoxazol-5-yl | SO₂CH₃ | H | C₂H₅ | H |

Also very particularly preferred are the compounds Ib, in particular the compounds Ib.1 to Ib.47, which differ from the compounds Ia.1 to Ia.47 only by the fact that they are present as the sodium salt:

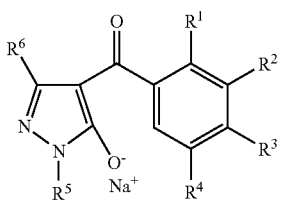

Ib

Also very particularly preferred are the compounds Ic, in particular the compounds Ic.1 to Ic.47, which differ from the compounds Ia.1 to Ia.47 only by the fact that they are present as the lithium salt:

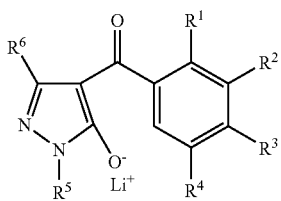

Ic

Also very particularly preferred are the compounds Id, in particular the compounds Id.1 to Id.47, which differ from the compounds Ia.1 to Ia.47 only by the fact that they are present as the potassium salt:

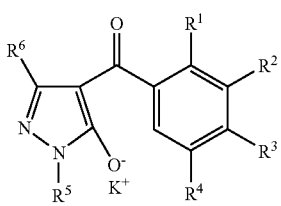

Id

Also very particularly preferred are the compounds Ie, in particular the compounds Ie.1 to Ie.47, which differ from the compounds Ia.1 to Ia.47 only by the fact that they are present as the ammonium salt:

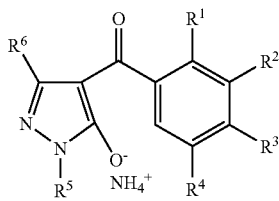

Ie

Very particularly preferred are, especially, the compounds Ia, especially the compounds Ia.1 to Ia.47.

Very particularly preferred are, moreover, the 3-heterocyclyl-substituted benzoyl derivatives of the formula I, where
R⁴ is hydrogen.

Very particularly preferred are, moreover, the 3-heterocyclyl substituted benzoyl derivatives of the formula I where
R² is a heterocyclic radical selected from the group: isoxazol-3-yl, isoxazol-4-yl and isoxazol-5-yl, it being possible for the three radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio.

Very particularly preferred are, especially, the 3-heterocyclyl-substituted benzoyl derivatives of the formula I, where
R² is isoxazol-3-yl which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
R⁴ is hydrogen.

Very particularly preferred are also, especially, the 3-heterocyclyl-substituted benzoyl derivatives of the formula I where
R² is isoxazol-5-yl, which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
R⁴ is hydrogen.

Most particularly preferred is 4-[2-chloro-3-(3-methylisoxazol-5-yl)-4-methylsulfonyl-benzoyl]-1-methyl-5-hydroxy-1H-pyrazole.

Most particularly preferred is also 4-[2-methyl-3-(3-methylisoxazol-5-yl)-4-methylsulfonyl-benzoyl]-1-methyl-5-hydroxy-1H-pyrazole.

Very particularly preferred are, moreover, the 3-heterocyclyl-substituted benzoyl derivatives of the formula I where $R^2$ is a heterocyclic radical selected from the group: 4,5-dihydroisoxazol-3-yl, 4,5-dihydroisoxazol-4-yl and 4,5-dihydroisoxazol-5-yl, it being possible for the three radicals mentioned to be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio.

Very particularly preferred are, especially, the 3-heterocyclyl-substituted benzoyl derivatives of the formula I where $R^2$ is 4,5-dihydroisoxazol-3-yl which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^4$ is hydrogen.

Most particularly preferred are the 3-heterocyclyl-substituted benzoyl derivatives of the formula I where $R^1$ is halogen or $C_1$-$C_6$-alkyl; and $R^2$ is 4,5-dihydroisoxazol-3-yl which can be unsubstituted or mono- or polysubstituted by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;

$R^3$ is $C_1$-$C_6$-alkylsulfonyl;

$R^4$ is hydrogen.

Most especially preferred is 4-[2-chloro-3-(4,5-dihydroisoxazol-3-yl)-4-methylsulfonylbenzoyl]-1-methyl-5-hydroxy-1H-pyrazole.

Most particularly preferred is also 4-[2-methyl-3-(4,5-dihydroisoxazol-3-yl)-4-methylsulfonyl-benzoyl]-1-methyl-5-hydroxy-1H-pyrazole.

With a view to the synergistic herbicidal action of the mixtures comprising a component A), B) and C) according to the invention, compounds from amongst groups C1 to C3 are preferred.

In particular, compounds from amongst the classes of active ingredients mentioned below are preferred, or the following compounds are very particularly preferred:

C1 acetolactate synthase inhibitors (ALS):
imidazolinones, in particular imazapyr, imazaquin, imazamethabenz, imazethapyr or imazamox, preferably imazapyr;
pyrimidyl ethers, in particular pyrithiobac sodium;
sulfonamides, in particular florasulam, flumetsulam or metosulam, preferably metosulam; or
sulfonylureas, in particular halosulfuron-methyl, primisulfuron-methyl, prosulfuron, rimsulfuron, thifensulfuron-methyl, tribenuron-methyl, N-[[[4-methoxy-6-(trifluoromethyl)-1,3,5-triazin-2-yl]-amino]carbonyl]-2-(trifluoromethyl)-benzene-sulfonamide or sulfosulfuron;

C2 lipid biosynthesis inhibitors:
anilides, such as anilofos or mefenacet;
chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor; in particular dimethenamid, S-dimethenamid, acetochlor, metolachlor or S-metolachlor;

C3 photosynthesis inhibitors:
pyridate or pyridafol, in particular pyridate;
benzothiadiazinones, in particular bentazone;
dipyridylenes, in particular paraquat-dichloride;
ureas, in particular diuron or isoproturon, preferably diuron;
phenols, in particular bromoxynil;
chloridazone;
triazines, in particular atrazine or terbutylazine; or
triazinones, in particular metribuzin.

In particular, compounds from amongst the classes of active ingredients mentioned below are preferred, or the following compounds are very particularly preferred.

C1 sulfonylureas:
amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, N-[[[4-methoxy-6-(trifluoromethyl)-1,3,5-triazin-2-yl]amino]carbonyl]-2-(trifluoromethyl)-benzenesulfonamide, sulfosulfuron or iodosulfuron, in particular rimsulfuron;

C2 lipid biosynthesis inhibitors, for example
chloroacetanilides, in particular dimethenamid, S-dimethenamid, acetochlor, metolachlor or S-metolachlor; in particular dimethenamid or S-dimethenamid;

C3 photosynthesis inhibitors:
pyridate;
benzothiadiazinones, in particular bentazone;
dipyridylenes, in particular paraquat-dichloride;
ureas, in particular diuron or isobroturon, preferably diuron;
phenols, in particular bromoxynil;
chloridazon;
triazines, in particular atrazine or terbutylazine; or
triazinones, in particular metribuzin.

Especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a sulfonylurea, in particular rimsulfuron.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a chloroacetanilide, in particular dimethenamid or S-dimethenamid.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a triazine, in particular atrazine.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a benzothiadiazinone, in particular bentazone.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a acetolactate synthase inhibitor, in particular a sulfonylurea, and a photosynthesis inhibitor, in particular a triazine.

Extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C rimsulfuoron and atrazine.

Also especially preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C a lipid biosynthesis inhibitor, in particular a chloracetanilide and a photosynthesis inhibitor, in particular a triazine.

Extraordinary preferred are synergistic herbicidal mixtures which comprise as component A 4-[2-methyl-3-(4,5-dihydroisoxazol-3-yl)-4-methylsulfonyl-benzoyl]-1-methyl-5-hydroxy-1H-pyrazole, as component B the compound of formula II and as component C dimethenamid and atrazine, or S-dimethenamid and atrazine.

The present invention also extends to herbicidal compositions which comprise a herbicidally active amount of a synergistic herbicidal mixture (comprising components A), B) and C) as described above), at least one liquid and/or solid carrier and, if desired, at least one surfactant.

The herbicidal compositions and synergistic herbicidal mixtures according to the invention can effect very good control of broad-leaved weeds and grass weeds in crops such as maize, cereals, rice and soya without damaging the crop plants, an effect observed especially even at low rates of application.

Taking into consideration the variety of application method in question, the herbicidal compositions and synergistic herbicidal mixtures according to the invention can additionally be employed in a further number of crop plants for eliminating undesirable plants. Examples of suitable crops are the following: *Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica) , Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N. rustica), Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* und *Zea mays.*

Moreover, the herbicidal compositions and synergistic herbicidal mixtures according to the invention can also be used in crops which tolerate the action of herbicides due to breeding, including genetic engineering methods.

The mixtures according to the invention, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The use forms depend on the intended purposes; in any case, they should guarantee the finest possible distribution of the active ingredients according to the invention.

Suitable inert auxiliaries are mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalene-sulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalene-sulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the synergistic herbicidal mixture or the individual active ingredients with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the mixtures according to the invention in the ready-to-use products can be varied within wide ranges. In general, the formulations comprise from 0.01 to 95% by weight, preferably 0.5 to 90% by weight, of the mixture according to the invention.

The components A) and B) and C) can be formulated jointly, but also separately, and/or applied to the plants, their environment and/or seeds jointly or separately. It is preferable to apply the active ingredients simultaneously. However, it is also possible to apply them separately.

Moreover, it may be advantageous to apply the herbicidal compositions and synergistic herbicidal mixtures according to the invention, jointly or separately, with additional other crop protection agents, for example with further herbicides and/or safeners and/or pesticides and/or agents for controlling phytopathogenic fungi or bacteria. Also of interest is the miscibility with mineral salt solutions which are employed for treating nutritional and trace element deficiencies. Non-phytotoxic oils and oil concentrates can also be added. The additional herbicide may be selected from the from the group of the acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.

The mixtures according to the invention and the herbicidal compositions can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal compositions according to the invention are preferably applied by foliar application. Application may be effected, for example, by usual spraying techniques with water as the carrier, using amounts of spray mixture of approx. 100 to 1000 l/ha. The compositions may also be applied by the so-called "low-volume" and "ultra-low-volume" methods, or in the form of so-called granules.

As a rule, the synergistic herbicidal mixtures comprise components A), B) and C) in such weight ratios that the synergistic effect takes place.

The ratios of component A) and B) in the mixture preferably range from 1:0.001 to 1:500, preferably from 1:0.01 to 1:100, particularly preferably from 1:0.1 to 1:50.

The ratios of components A) and C) in the mixture preferably range from 1:0.002 to 1:800, preferably from 1:0.003 to 1:250, particularly preferably from 1:0.003 to 1:160, especially from 1:0.02 to 1:250, especially preferably from 1:0.02 to 1:160.

The rate of application of pure synergistic herbicidal mixture, i.e. without formulation auxiliaries, amounts to 0.2 to 5000 g/ha, preferably 2 to 2000 g/ha, in particular 8 to 1000 g/ha, of active substance (a.s.), depending on the intended aim, the season, the target plants and growth stage.

The rate of application of 3-heterocyclyl-substituted benzoyl derivative of the formula I is 0.1 to 250 g/ha, as a rule 5 to 250 g/ha, preferably 10 to 150 g/ha, of active substance (a.s.).

The preferred rate of application of the compound of formula II is 0.1 to 250 g/ha, as a rule 1 to 120 g/ha, preferably 10 to 100 g/ha, of active substance (a.s.)

The preferred application rate of the active ingredients of the optional component C are compiled in Table 2.

TABLE 2

| Component C | | Class of active ingredient | Active ingredient | Rate of application (g/ha) |
|---|---|---|---|---|
| C1 | acetolactate synthase inhibitors (ALS) | | | 0.2-800 |
| | | imidazolinones | | 0.2-800 |
| | | | imazapyr | 0.3-400 |
| | | | imazaquin | 0.5-300 |
| | | | imazamethabenz | 1-800 |
| | | | imazapic | 0.2-400 |
| | | | imazethapyr | 0.3-150 |
| | | | imazamox | 0.2-120 |
| | | pyrimidyl ethers | | 2-120 |
| | | | pyrithiobac-sodium | 2-120 |
| | | sulfonamides | | 1-225 |
| | | | florasulam | 1-20 |
| | | | flumetsulam | 25-225 |
| | | | metosulam | 1-60 |
| | | sulfonylureas | | 1-120 |
| | | | halosulfuron-methyl | 5-120 |
| | | | primisulfuron-methyl | 10-120 |
| | | | prosulfuron | 10-120 |
| | | | rimsulfuron | 5-120 |
| | | | thifensulfuron-methyl | 10-60 |
| | | | tribenuron-methyl | 10-60 |
| | | | N-[[[4-methoxy-6-(trifluoro-methyl)-1,3,5-triazin-2-yl]-amino]carbonyl]-2-(trifluoro-methyl)-benzene-sulfonamide | 5-120 |
| | | | sulfosulfuron | 10-60 |
| C2 | lipid biosynthesis inhibitors | | | 60-4000 |
| | | chloroacet-anilides | | 60-4000 |
| | | | dimethenamid | 60-2000 |
| | | | S-dimethenamid | 60-2000 |
| | | | acetochlor | 250-4000 |
| | | | metolachlor | 60-4000 |
| | | | S-metolachlor | 60-4000 |
| | | thioureas | | 100-4000 |
| | | | benthiocarb | 1000-4000 |
| C3 | photosynthesis inhibitors | | | 30-4000 |
| | | — | pyridate | 250-1500 |
| | | | pyridafol | 250-1000 |
| | | benzothia-diazinones | | 250-1440 |
| | | | bentazone | 250-1440 |
| | | dipyridylenes | | 100-800 |
| | | | paraquat-dichloride | 100-800 |
| | | ureas | | 250-1600 |
| | | | diuron | 250-1600 |
| | | | isoprotoron | 250-1600 |
| | | phenols | | 100-700 |
| | | | bromoxynil | 100-700 |
| | | chloridazon | | 500-4000 |
| | | triazines | | 125-4000 |
| | | | atrazine | 125-4000 |
| | | | terbutylazine | 125-4000 |
| | | triazinone | | 30-300 |
| | | | metribuzin | 30-300 |

USE EXAMPLES

The mixtures according to the invention were applied pre- or post-emergence (foliar treatment). The herbicidal compounds of component B and of component C were applied in the formulation in which they are present as commercially available product.

The herbicidally active compounds of components A), B) and C) were applied in succession or jointly, in the latter case in some cases as a tank mix and in some cases as a readymix, in the form of emulsions, aqueous solutions or suspensions, the vehicle being water (300-400 l/ha). In the case of the field trials, application was effected with the aid of a mobile plot sprayer.

The test period extended over 3 to 8 weeks, and the stands were also observed at later points in time.

Damage by the herbicidal compositions was evaluated with reference to a scale of 0% to 100% in comparison with untreated control plots. 0 means no damage and 100 means complete destruction of the plants.

The following examples will demonstrate the action of the herbicidal compositions which can be used according to the invention, without excluding the possibility of other uses.

In these examples, the value E at which only an additive effect of the individual active ingredients is to be expected was calculated by the method of S. R. Colby (Calculating synergistic and antagonistic responses of herbicide combinations, Weeds 15, 20 pp (1967)).

This was done using the formula $$E = X + Y - \frac{XY}{100}$$

where

X=Percentage of the herbicidal action of component X) at an application rate of x;

Y=Percentage of the herbicidal action of component Y) at an application rate of y;

E=expected herbicidal action of component X)+Y) at rates of application x+y (in %).

If the value observed exceeds the value E calculated in accordance with Colby's formula, then synergism is present.

The herbicidal mixtures according to the invention exert a greater herbicidal action than would have been expected according to Colby on the basis of the observed effects of the individual components when used alone.

The results of the tests are shown in Tables 3 to 4 below. In these studies, the following plants were used:

| Scientific name | Common name |
| --- | --- |
| Anoda cristata | Anodaweed |
| Sorghum halepense | Johnsongrass |
| Tagetes minuta | Wild marigold |

TABLE 3

Herbicidal action of compound 1a.29, nicosulfuron and atrazine (post-emergence treatment; field trail)

| | Application rate [g/ha ai] | Anoda cristata Damage [%] | Colby Value E | Tagetes minuta Damage [%] | Colby Value E |
| --- | --- | --- | --- | --- | --- |
| Ia.29 + nicosulfuron | 40 + 20 | 89 | — | 84 | — |
| atrazine | 1250 | 70 | | 50 | — |
| Ia.29 + nicosulfuron + atrazine | 40 + 20 + 1250 | 100 | 97 | 100 | 92 |

TABLE 4

Herbicidal action of compound 1a.29, nicosulfuron and atrazine (post-emergence treatment; field trail)

| | Application rate [g/ha ai] | Sorghum halepense Damage [%] | Colby Value E |
| --- | --- | --- | --- |
| Ia.29 + nicosulfuron | 47.04 + 20.25 | 40 | — |
| atrazine | 1250 | 10 | — |
| Ia.29 + nicosulfuron + atrazine | 47.04 + 20.25 + 1250 | 65 | 46 |

We claim:

1. A synergistic herbicidal mixture comprising
   A) 4-[2-methyl-3-(4,5-dihydroisoxazol-3-yl)-4-methylsulfonyl-benzoyl]-1-methyl-5-hydroxy-1H-pyrazole or one of its environmentally compatible salts;
   B) nicosulfuron (II) or one of its environmentally compatible salts; and,
   C) at least one herbicidal compound from the group triazines or one of their environmentally compatible salts, wherein said triazine is selected from the group consisting of ametryn, atrazine, cyanazine, desmetryn, dimethamethryn, prometon, prometryn, propazine, simazine, simetryn, terbumeton, terbutryn, terbutylazine and trietazine; in a synergistically effective amount.

2. A synergistic herbicidal mixture as claimed in claim 1, comprising as component A) 4-[2-methyl-3-(4,5-dihydroisoxa-zol-3-yl)-4-methylsulfonyl-benzoyl]-1-methyl-5-hydroxy-1H-pyrazole or one of its environmentally compatible salts, as component B) nicosulfuron (II) or one of its environmentally compatible salts and as component C) atrazine or one of its environmentally compatible salts.

3. A synergistic herbicidal mixture as claimed in claim 1, wherein component A) and B) are present in a weight ratio of 1:0.001 to 1:500.

4. A synergistic herbicidal mixture as claimed in claim 1, wherein component A) and component C) are present in a weight ratio of 1:0.002 to 1:800.

5. A herbicidal composition comprising a herbicidally active amount of a synergistic herbicidal mixture as claimed in claim 1 and, at least one inert liquid and/or solid carrier and, if desired, at least one surfactant.

6. A process for preparing a herbicidal composition of claim 5, comprising mixing component A), component B) and component C) and, at least one liquid and/or solid carrier and, if appropriate, a surfactant.

7. The mixture according to claim 1, wherein A) is present in an amount which results in an application rate of 0.1 to 250 g/ha, B) is present in an amount which results in an application rate of 0.1 to 250 g/ha, and C) is present in an amount which results in an application rate of 125-4000 g/ha.

8. A method of controlling undesired vegetation, comprising applying before, during or after the emergence of the undesired vegetation, either simultaneously or separately, a synergistic herbicidal combination of
- A) 4-[2-methyl-3-(4,5-dihydroisoxazol-3-yl)-4-methylsulfonyl-benzoyl]-1-methyl-5-hydroxy-1H-pyrazole or one of its environmentally compatible salts;
- B) nicosulfuron (II) or one of its environmentally compatible salts; and,
- C) at least one herbicidal compound from the group of triazines or one of their environmentally compatible salts, wherein said triazine is selected from the group consisting of ametryn, atrazine, cyanazine, desmetryn, dimethamethryn, prometon, prometryn, propazine, simazine, simetryn, terbumeton, terbutryn, terbutylazine and trietazine; in a synergistically effective amount.

9. The method of claim 8, wherein the undesired vegetation is proximate crop plants, and the synergistic herbicidal combination is applied to the leaves of the crop plants and of the undesired plants.

* * * * *